(12) United States Patent
Patel

(10) Patent No.: US 8,389,502 B2
(45) Date of Patent: *Mar. 5, 2013

(54) STABILIZED STEROID COMPOSITION AND METHOD FOR ITS PREPARATION

(75) Inventor: Pravin M. Patel, Bloomfield Hill, MI (US)

(73) Assignee: Precision Dermatology, Inc., Cumberland, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/155,493

(22) Filed: Jun. 8, 2011

(65) Prior Publication Data

US 2011/0237811 A1    Sep. 29, 2011

Related U.S. Application Data

(63) Continuation of application No. 11/432,742, filed on May 11, 2006, now Pat. No. 7,981,877, which is a continuation-in-part of application No. 10/762,652, filed on Jan. 22, 2004, now Pat. No. 7,378,405.

(60) Provisional application No. 60/442,114, filed on Jan. 23, 2003.

(51) Int. Cl.
*A61K 31/56* (2006.01)

(52) U.S. Cl. ...................................... 514/170

(58) Field of Classification Search ................... 514/182
See application file for complete search history.

(56) References Cited

U.S. PATENT DOCUMENTS

| 4,344,940 | A | 8/1982 | Chow et al. |
| 5,496,565 | A | 3/1996 | Heinze et al. |
| 5,650,156 | A | 7/1997 | Grinstaff et al. |
| 5,665,383 | A | 9/1997 | Grinstaff et al. |
| 5,968,519 | A | 10/1999 | Youssefyeh et al. |
| 6,090,800 | A | 7/2000 | Unger et al. |
| 6,245,340 | B1 | 6/2001 | Youssefyeh |
| 7,378,405 | B2 * | 5/2008 | Patel ............................. 514/180 |
| 7,981,877 | B2 * | 7/2011 | Patel ............................. 514/182 |

OTHER PUBLICATIONS

Remington Pharaceutical Sciences; Eighteenth Edition; 1990; pp. 956-971.

* cited by examiner

*Primary Examiner* — San-Ming Hui
(74) *Attorney, Agent, or Firm* — Foley Hoag LLP

(57) ABSTRACT

Stabilized, 17-substituted hydrocortisone containing compositions and methods of manufacture are disclosed. Isomerization of the hydrocortisone component of topical steroid compositions is markedly reduced by including an omega-6 acid component in the form of a free acid or as a compound such as an ester. Specifically disclosed are methods for preventing the isomerization of hydrocortisone 17-butyrate into hydrocortisone 21-butyrate through the use of safflower oil.

9 Claims, No Drawings

STABILIZED STEROID COMPOSITION AND METHOD FOR ITS PREPARATION

RELATED APPLICATIONS

This application is a continuation of U.S. patent application Ser. No. 11/432,742 filed May 11, 2006, which is a continuation-in-part of U.S. patent application Ser. No. 10/762,652 filed Jan. 22, 2004, which claims priority of U.S. Provisional Patent Application Ser. No. 60/442,114 filed Jan. 23, 2003, which is incorporated herein by reference.

FIELD OF THE INVENTION

This invention relates generally to stabilized steroid compositions. More specifically, the invention relates to compositions and methods for stabilizing hydrocortisone compounds. Still more specifically, the invention relates to methods for stabilizing 17-substituted hydrocortisone compounds. Most specifically, the invention relates to methods and compositions for stabilizing hydrocortisone 17-butyrate.

BACKGROUND OF THE INVENTION

Hydrocortisone compounds have a very strong anti-inflammatory effect on many tissues. Consequently, these materials are often employed as topical agents for the relief of various inflammations. Hydrocortisone esters are one preferred class of steroidal anti-inflammatory agents, and hydrocortisone 17-butyrate (HC17-B) is one particularly preferred hydrocortisone material which is in widespread use as a therapeutic agent.

In this description, conventional IUPAC numbering will be followed for steroid molecules. Shown below is the molecular structure of HC17-B. As can be seen, the butyrate moiety is joined to the molecule at the 17 position.

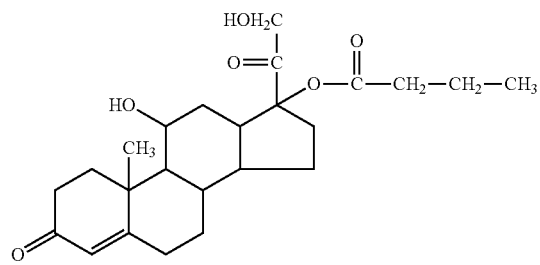 [SMILES: CCCC(=O)OC1(C(=O)CO)CCC2C3CCC4=CC(=O)CCC4(C)C3C(O)CC21]

One problem which has been encountered in connection with HC17-B formulations is that the molecule is prone to rearrange so as to form an isomer in which the butyrate group is attached to the remainder of the molecule through the 21 position. This isomer is generally referred to as HC21-B. Similar rearrangements occur in other hydrocortisone 17-esters.

This isomerization reaction is generally enhanced when materials such as HC17-B are in a solution or dispersion, as they usually are in a pharmaceutical formulation such as a topical lotion or cream. Isomerization is of particular concern to pharmaceutical formulators since the isomerization reaction raises therapeutic and regulatory issues regarding the efficacy and composition of isomerized compositions. Therefore, the pharmaceutical industry has sought methods and materials whereby steroid compositions such as HC17-B can be stabilized against isomerization or other degradation. However, any such methods or materials should be compatible with the intended therapeutic utility of the hydrocortisone composition; and in this regard, resultant compositions should be effective and nontoxic. Ideally, any such method should employ materials which have previously been demonstrated to be safe.

As will be explained hereinbelow, the present invention provides materials and methods for inhibiting the degradation of HC17-B and the like. The materials and methods of the present invention are easy to implement, low in cost, safe, and are compatible with pharmaceutical compositions and methods of the type generally employed in connection with hydrocortisone containing agents.

SUMMARY OF THE INVENTION

Disclosed and claimed herein is a method of stabilizing 17-substituted hydrocortisone compounds, as well as the stabilized 17-substituted hydrocortisone compounds themselves. The method comprises the step of adding a quantity of an omega-6 acid, either in free form or as a compound such as an ester, to a 17-substituted hydrocortisone composition.

In a particularly preferred embodiment of the method of the present invention, the omega-6 acid comprises linoleic acid. Since safflower oil is a triglyceride which includes an ester of linoleic acid, the omega-6 acid component may be added to the 17-substituted hydrocortisone composition in the form of safflower oil. Safflower oil is, itself, an effective emollient and enhances the skin treatment properties of the stabilized composition. In a particularly preferred embodiment, the safflower oil is added to the hydrocortisone composition in an amount such that the linoleic acid component is present in an at least equimolar proportion to the hydrocortisone. It has been found that it is highly desirable to add the safflower oil to the composition at a weight percent which is in considerable excess to the weight percent of the hydrocortisone, such as ten, twenty, thirty or more times as much.

Practicing the method of the present invention, the 17-substituted hydrocortisone may comprise hydrocortisone 17-butyrate.

In addition to the 17-substituted hydrocortisone and omega-6 acid, the composition of the present invention may further comprise a number of other compounds typically found in pharmacological hydrocortisone creams and lotions, such as various alcohols, mineral oil, white petroleum, preservative such as BHT, propylparaben and/or butylparaben, citric or other mild acids, sodium citrate, glycerin, fragrances, coloring agents, etc. Generally speaking, the majority of the composition of the present invention will constitute purified water.

DETAILED DESCRIPTION OF THE INVENTION

In accord with the present invention, it has been unexpectedly found that the presence of an omega-6 acid component, comprising either the free acid or a derivative thereof such as an ester or the like ("omega-6 acid component"), will inhibit the isomerization of 17-substituted hydrocortisones and other steroid materials. The present invention has particular utility in the stabilization of hydrocortisones having an ester moiety at the 17 position, and is particularly useful in stabilizing HC17-B, and will be described with particular reference to the stabilization of HC17-B.

There are a variety of omega-6 acids which function to stabilize the substituted hydrocortisones. "Omega-6" signifies that the first double bond in the acid, counting from the end opposite the acid group, occurs in the sixth carbon-carbon bond. There is some confusion due to the fact that there are various nomenclature and numbering systems used for fatty acids. Hence materials of the present invention have been referred to as "omega-3" acids, as well as by other names. In any event, within the context of this disclosure, the foregoing definition of omega-6 acids is utilized. Linoleic acid, also known as 9,12-octadecadienoic acid, is one omega-6 acid having utility in the present invention. Linoleic acid is generally a very safe material, and is readily available. Safflower oil is a triglyceride, comprising a fatty acid ester of glycerol, and it contains large amounts of linoleic acid in esterified form, and in particular embodiments of the present invention, safflower oil is used as a stabilizing agent for HC17-B and similar materials. Safflower oil is particularly advantageous for use in pharmaceutical compositions, since it is generally nontoxic, and has been approved for both topical and internal formulations. Additionally, safflower oil, as well as other omega-6 acid materials, have additional beneficial effects in topical formulations since they can enhance skin penetration and restore lipid content to the skin.

Other omega-6 acids include arachidonic acid. Yet other polyunsaturated omega-6 acids are known in the art. Such omega-6 acids, as well as their esters and like compounds, may also be used in the present invention.

In general, the omega-6 acid component will be present in an amount which is at least equimolar with the steroid compound which is to be stabilized. In most practical formulations, the omega-6 acid component is present in a relatively large excess, since it further functions as a skin conditioning agent. For example, it may be present in a weight percentage ten, twenty, thirty or even more times the weight percentage of the steroid compound.

EXAMPLE

Two experimental hydrocortisone 17-butyrate formulations were prepared. One (formulation R6546) contained a substantial weight percentage (3.0% w/w) of refined safflower oil. The other formulation (R6539) was similar in composition to the first formulation, but lacked any safflower oil. In both formulations, the HC17-B was present in a weight percentage of 0.1. Table 1 shows, respectively, the recipes for the two formulations, showing the various components respectively thereof as weight percentages.

TABLE 1

| R6546 | | R6539 | |
|---|---|---|---|
| Ingredient | %, w/w | Ingredient | %, w/w |
| Ceteth-20 | 2.0 | Ceteth-20 | 2.0 |
| Cetostearyl alcohol | 4.0 | Cetostearyl alcohol | 4.0 |
| White petrolatum | 2.5 | White petrolatum | 2.5 |
| Light mineral oil | 5.5 | Light mineral oil | 7.5 |
| Safflower oil | 3.0 | Propylparaben | 0.1 |
| BHT | 0.02 | Butylparaben | 0.05 |
| Propylparaben | 0.1 | Hydrocortisone 17-butyrate | 0.1 |
| Butylparaben | 0.05 | Citric acid | 0.42 |
| Hydrocortisone 17-butyrate | 0.1 | Sodium citrate (dehydrate) | 0.32 |
| Citric acid | 0.42 | Purified water | 83.01 |
| Sodium citrate (dehydrate) | 0.32 | | |
| Purified water | 81.99 | | |

Table 2 shows the analytic results of samples of the resultant respective compositions, showing the exact percentages of the HC 17-B (as well as propylparaben and butylparaben) found in the two formulations expressed as weight percentages.

TABLE 2

| | | HCB (%, w/w) | Propylparaben (%, w/w) | Butylparaben (%, w/w) |
|---|---|---|---|---|
| R6539 | Sample #1 | 0.104 | 0.104 | 0.052 |
| | Sample #2 | 0.103 | 0.103 | 0.051 |
| | Average | 0.104 | 0.104 | 0.052 |
| R6546 | Sample #1 | 0.100 | 0.102 | 0.051 |
| | Sample #2 | 0.101 | 0.102 | 0.050 |
| | Average | 0.101 | 0.102 | 0.051 |

From Table 2, it can be ascertained that the formulation containing the safflower oil had an average weight percentage of 0.101 HC17-B, whereas the sample which did not contain the safflower oil had an average weight percentage of HC17-B of 0.104, a slightly greater weight percentage.

The stability of the respective formulations was tested by analyzing the two formulations over a six-month period, at various intervals. The stability study was performed at a temperature of 40° Centigrade, considerably greater than normal room temperature.

TABLE 3

| | | HCB (%, w/w) | Propyl-paraben (%, w/w) | Butyl-paraben (%, w/w) | HC21-B (%) | Other impurities (%) |
|---|---|---|---|---|---|---|
| R6539 | 1-month | 0.102 | 0.103 | 0.052 | 0 | 0 |
| | 2-month | 0.100 | 0.101 | 0.051 | 0 | 0 |
| | 3-month | 0.095 | 0.100 | 0.050 | — | — |
| | 6-month | 0.086 | 0.100 | 0.050 | 6.36 | 2.81 |
| R6546 | 1-month | 0.103 | 0.103 | 0.051 | 0 | 0 |
| | 2-month | 0.101 | 0.102 | 0.052 | 0 | 0 |
| | 3-month | 0.099 | 0.103 | 0.051 | 2.51 | 0.45 |
| | 6-month | 0.095 | 0.102 | 0.052 | 5.00 | 0.56 |

As can be readily ascertained by comparing the six-month results for the two compositions, the composition containing the safflower oil (R6546) did lose some HC17-B. The weight percentage went from 0.101 at the start of the study (from Table 2) to 0.095 after six months. Furthermore, the isomer HC21-B began to make its appearance at the three-month interval, and was found at the six-month endpoint of the study in a concentration of 5.00 weight percent of the HC17-B content. Furthermore, there were various other impurities found at the six-month endpoint in a percentage of 0.56 weight percent.

In contrast, the formulation which did not contain the safflower oil (R6539), although starting out containing slightly more HC17-B, it lost this component more rapidly and wound up with a considerably lower weight percentage of 0.86 at the six-month endpoint of the study. As would be expected, the formulation without the safflower oil and its constituent linoleic acid contained an even larger percentage of the isomer HC21-B, namely, 6.36%. Furthermore, other impurities were found in this formulation after six months in a much larger percentage as well, namely, 2.81 weight percent as compared to only 0.56 weight percent.

As can be seen from this data, adding the omega-6 acid component in the form of the linoleic acid-containing safflower oil considerably increased the stability of the valuable hydrocortisone 17-butyrate compound. In fact, the formulation which did not contain the safflower oil lost approximately 18% of its original HC17-B, whereas the formulation containing the safflower oil lost only approximately 6%. In other words, the improvement in stability was practically threefold. Furthermore, the level of the HC21-B isomer and the other impurities was about 60% less in the formulation containing the safflower oil than in the formulation where the safflower oil was absent.

Thus, adding an omega-6 acid component in the form of safflower oil has been shown to be an effective way of stabilizing 17-substituted hydrocortisone compounds. While the methods and compositions of the present invention have been described with reference to certain exemplifications and embodiments thereof, the invention is by no means limited to the specifically depicted examples and embodiments. For example, other 17-substituted hydrocortisone compounds could also be stabilized through the use of the present invention. The omega-6 acid component could be provided in other forms than as linoleic acid generally, or as safflower oil specifically. It is only necessary that the omega-6 acid component be provided in a form which is pharmacologically compatible with topical hydrocortisone creams and lotions. Doubtless, one of skill in the art could, after routine experimentation, employ other pharmacologically compatible omega-6 components with similar efficacy without departing from the scope of the present invention. It is the claims appended hereto, rather than the exact exemplifications and embodiments, which define the scope of the present invention.

The invention claimed is:

1. A method for stabilizing a composition including a 17-substituted hydrocortisone therein, said method comprising the step of:
    adding a stabilizer to said composition, said stabilizer comprising an omega-6 acid or an ester of an omega-6 acid.

2. The method of claim 1, wherein said step of adding said stabilizer comprises adding linoleic acid to said composition.

3. The method of claim 1, wherein said step of adding said stabilizer to said composition comprises adding a triglyceride which includes an ester of said omega-6 acid to said composition.

4. The method of claim 3, wherein said triglyceride comprises safflower oil.

5. The method of claim 1, wherein the step of adding said stabilizer further comprises adding said stabilizer in an amount so that the omega-6 acid component thereof is at least equimolar to a quantity of said 17-substituted hydrocortisone.

6. The method of claim 5, wherein the molar amount of the omega-6 acid component is substantially greater than the molar amount of said 17-substituted hydrocortisone.

7. A method for stabilizing a 17-substituted hydrocortisone compound, said method comprising the step of:
    disposing said hydrocortisone compound in a composition which includes a stabilizer comprising an omega-6 acid or an ester of an omega-6 acid.

8. The method of claim 7, wherein the stabilizer comprises safflower oil.

9. The method of claim 7, wherein the step of adding said stabilizer comprises adding said stabilizer in an amount so that the omega-6 acid component thereof is at least equimolar to a quantity of said 17-substituted hydrocortisone compound.

* * * * *